US006897058B2

(12) United States Patent
Švedas et al.

(10) Patent No.: US 6,897,058 B2
(45) Date of Patent: May 24, 2005

(54) METHOD FOR THE PREPARATION OF ENANTIOMERICALLY ENRICHED AMINES

(75) Inventors: Vytautas-Juozapas Kajetono Švedas, Moscow (RU); Dorel Teodor Guranda, Moscow (RU); Roger Arthur Sheldon, Rijswijk (NL); Frederik Rantwijk Van, Waddinxveen (NL); Lukas Michaël Langen Van, Delft (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 10/363,361

(22) PCT Filed: Aug. 30, 2001

(86) PCT No.: PCT/NL01/00642

§ 371 (c)(1),
(2), (4) Date: Jun. 24, 2003

(87) PCT Pub. No.: WO02/20820

PCT Pub. Date: Mar. 14, 2002

(65) Prior Publication Data

US 2004/0014181 A1 Jan. 22, 2004

(30) Foreign Application Priority Data

Sep. 8, 2000 (NL) .............................................. 1016126
Dec. 4, 2000 (NL) .............................................. 1016785

(51) Int. Cl.$^7$ .......................... C12N 9/80; C12P 13/02; C07C 231/00
(52) U.S. Cl. ....................... 435/280; 435/129; 435/228
(58) Field of Search ................................ 435/129, 227, 435/228, 280

(56) References Cited

U.S. PATENT DOCUMENTS 6,033,823 A * 3/2000 Van Der Laan et al. ..... 430/230
6,465,223 B1 * 10/2002 Nubling et al. ............. 435/128

FOREIGN PATENT DOCUMENTS

| EP | 0176068 | 4/1986 |
| NL | 1009814 | 2/2000 |
| NL | 1010506 | 5/2000 |
| WO | WO 94/02628 | 2/1994 |
| WO | WO 98/50575 | 11/1998 |

OTHER PUBLICATIONS

Guy et al. "Kinetic resolution of p–hydroxyphenyl acetamides by hydrolysis with Pen–G acylase" Bioorganic Med. Chem. Lett. (1993) 3(6): 1021–1044.*

Vedejs et al. "Heteroarene–2–sulfonyl chlorides (BtsCI; ThsCI): Reagents for nitrogen protection and >99% racemization–free phenylglycine activation with SOC12" J. Am. Chem. Soc. (1996) 118(4): 9796–9797.*
Bossi, A. et al., "Production of D–Phenylglycine from Racemic (D.L)–Phenylglycine via Isoelectrically–Trapped Penicillin G Acylase" Biotechnology and Bioengineering. Including: Symposium Biotechnology in Energy Production and Conservation 60(4):454–461 (1998).
Guranda, D.T. et al., "High Efficiency and Enantioselective Enzymatic Acylation of Amines in Aqueous Medium" Tetrahedron: Asymmetry 12(11):1645–1650 (2001).
Kajfez, F. et al., "A New Synthesis of Ampicillin and Related Investigations" Journal of Heterocyclic Chemistry 13(3):561–566 (1976).
Löffler, J. and Schobert, R., "2(3H)–Oxazolones from Alpha–Hydroxy Amides and Keteneylidenetriphenyl–Phosphorane Via Ylide Cascade" Liebigs Ann. Org. Bioorg. Chem. pp. 217–220 (1997).
Rossi, D. et al., "Approach to the Use of Benzyl Penicillin Acylase for Configurational Correlations of Amino Compounds" Journal of Organic Chemistry 43(13):2576–2581 (1978).
Svedas, V. et al., "Kinetic Study of Penicillin Acylase from Alcaligenes faecalis" FEBS Letters 417(3):414–418 (1997).
Van Langen, L.M. et al., "Penicillin Acylase–Catalyzed Resolution of Amines in Aqueous Organic Solvents" Tetrahedron: Asymmetry 11(22):4593–4600 (2000).

* cited by examiner

Primary Examiner—Jean C. Witz
Assistant Examiner—Susan Hanley
(74) Attorney, Agent, or Firm—Morrison & Foerster LLP

(57) ABSTRACT

Method for the preparation of an enantiomerically enriched acylated amine wherein a phenylacetic acid derivative is brought into contact with a mixture of enantiomers of an amine $H_2NCR_1R_2R_3$, in which $R_1$, $R_2$, $R_3$ are not equal to each other and each independently stand for H, CN, a whether or not substituted (cyclo)alkyl, ary-, alkylaryl or arylalkyl group, whether or not cyclic heteroalkyl or heteroaryl group with one or more N, O or S atoms or in which $R_1$ and $R_2$ (and $R_3$) together with the C-atom to which they have been bound form a (bi)cyclic group that optionally contains one or more N, O of S atoms, in the presence of a Pen-G acylase derived from *Alcaligenes faecalis*.

And method for the preparation of enantiomerically enriched amine of formula $H_2NCR_1R_2R_3$, in which $R_1$, $R_2$, $R_3$ are as defined above, wherein an acylated amine is brought into contact with a Pen-G acylase originating from *Alcaligenes faecalis*. Preferably enantiomerically enriched phenylglycine amide or an ester of p-hydroxyphenylglycine is applied as phenylacetic acid derivative.

20 Claims, No Drawings

METHOD FOR THE PREPARATION OF ENANTIOMERICALLY ENRICHED AMINES

CROSS-REFERENCE TO RELATED APPLICATION

This application is the national phase of PCT application PCT/NL01/00642 having an international filing date of 30 Aug. 2001, and claims priority from European applications NL 1016126 filed 8 Sept. 2000 and NL 1016785 filed 4 Dec. 2000. The contents of these documents are incorporated herein by reference.

The invention relates to a method for the preparation of an enantiomerically enriched acylated amine of formula 1,

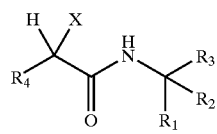

in which $R_4$ is a substituted or unsubstituted phenyl group, X stands for H, OH, $NH_2$, NHOH, F, Cl, Br, $NO_2$, alkyl or alkoxy with 1–3 C-atoms and $R_1$, $R_2$, $R_3$ are not equal to each other and each independently stand for H, CN, a substituted or unsubstituted (cyclo)alkyl, aryl, alkylaryl or arylalkyl group, cyclic or non-cyclic heteroalkyl or heteroaryl group with one or more N, O or S atoms, wherein a hphenylacetic acid derivative of formula 2,

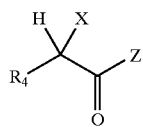

in which $R_4$ and X are as defined above, and in which Z stands for a C1–C7 alkoxy group; $NR_6R_7$, where $R_6$ and $R_7$ each independently stand for H, a substituted or unsubstituted (cyclo)alkyl, or aryl group; $NHNH_2$; $NHOR_8$, where R8 stands for H, or a C1–C7 alkyl group, is brought into contact with a mixture of enantiomers of the corresponding amine $H_2NCR_1R_2R_3$, where $R_1$, $R_2$ and $R_3$, are as defined above, in the presence of a Pen-G acylase originating from *Alcaligenes faecalis*.

The acylation of the compounds $H_2NCR_1R_2R_3$ with the aid of a Pen-G acylase has not been described in the literature. In D. Rossi et al in J.Org.Chem (1978), Vol. 43, No.13, 2576–2581, a description is given of the hydrolysis of compounds of formula 1 with the aid of a Pen-G acylase originating from *E. Coli*. Surprisingly however it has been found that when an enzyme originating from *Alcaligenes faecalis* is applied in the preparation of the amines as described above, in comparison with a Pen-G acylase from *E. Coli* a higher enantioselectivity can be achieved, both in the acylation of amines and in the hydrolysis of acylated amines. An additional advantage of the method according to the invention is that the enzyme originating from *Alcaligenes faecalis* has a higher stability at the high pH values that are optimal for the process. Surprisingly it has also been found that when an enzyme originating from *Alcaligenes faecalis* is applied a higher S/H ratio (ratio of synthesis of acylated product to hydrolysis of the phenylacetic acid derivative) can be achieved in the acylation. In addition it appeared that with the aid of enzymes originating from *Alcaligenes faecalis* a higher enzyme activity can also be achieved.

The invention also relates to a method for the preparation of an enantiomerically enriched amine via hydrolysis of a compound of formula 1. The (acylated) amines obtained by the method according to the invention preferably have an enantiomeric excess (ee)>90%, in particular >95%, more in particular >98%.

Enantiomerically enriched amines that can be prepared with the method according to the invention are amines of formula 1, where $R_1$, $R_2$, $R_3$, $R_4$ and X are as defined above. It will be clear that if the acyl donor also contains a chiral centre, the acylated amines of formula 1 are diastereomers. Enantiomerically enriched acylated amines of formula 1 within the framework of the present invention are therefore also understood to be such diastereomerically enriched acylated amines of formula 1, the enrichment relating in particular to the carbon atom which is bound to N, $R_1$, $R_2$ and $R_3$.

The (hetero)allcyl groups in R1, R2 and R3 preferably have 1–20, in particular 1–10 C-atoms; the (hetero)cycloallcyl, (hetero)aryl, (hetero)alkylaryl, (hetero)arylalkyl groups preferable have 3–20, in particular 3–12 C-atoms. They can be substituted with for example 1 or more halogens, hydroxy, alkoxy, aryloxy, tbio, alkylthio, arylthio, cyano, nitro, amino, (di)alkylamino, or amido groups. Preferably at least one of the groups $R_1$, $R_2$ and $R_3$ represents a (hetero)aryl, -aralkyl- or -alkaryl group. The alkylpart of the aralkyl or alkarylgroup is preferably 1–3 C-atoms and the aryl group is preferably a phenylgroup, which may be substituted with for example hydroxy, alkoxy, halogen or nitro. A specially suited group of compounds, for use in the present invention is the group of enantiomerically enriched acylated amines according to formula 1 or of the corresponding amine $H_2NCR_1R_2R_3$, wherein $R_1$ is chosen from the group of $CH_3OH$, $CH_3$, $R_2$ is chosen from the group of H, $CH_3$ and $R_3$ is chosen from the group of alkyl, preferably with 2–4 C-atoms, aralkyl, in which the alkyl part is preferably 1–3 C-atoms and in which the arylgroup is preferably a phenylgroup, which may be substituted with for example hydroxy, alkoxy, halogen or nitro. Amines that are specially suitable to be prepared or split with the aid of the method according to the invention are for example phenylalkylamines, in particular 1-phenyl-ethylamine, 1-(p-Cl-phenyl)-ethylamine, 1-(1-naphthyl) ethylamine, 1-(2-naphthyl)-ethylamine, 2-amino-4-phenylbutane, 1,1,1-trifluoro-2-amino-3-phenylpropane, 1-phenyl-1-amnio-2-ethanol. Possible substituents on the phenyl group in $R_4$ are for example, hydroxy, alkoxy, halogen or nitro.

As phenylacetic acid derivatives (acyl donor) in the method according to the invention for example a substituted or unsubstituted amide or an alkyl ester of a (substituted) acetic acid is applied, preferably phenylacetic acid amide, phenylacetic acid methyl ester or phenylglycine amide. If the phenylacetic acid derivative contains a chiral centre, preferably the phenylacetic acid derivative is applied in an as high as possible enantiomeric purity, for example an ee (enantiomeric excess)>90%, preferably >95%, in particular >98%.

Preferably phenylglycine amide or an ester of p-hydroxyphenylglycine is applied as acyl donor. An additional advantage of application of phenylglycine amide or an ester of p-hydroxyphenylglycine as acyl donor is that in most cases the acylated amines of formula 1 are crystalline products. This means that compounds which are not completely diastereomerically pure can be purified via a simple crystallization step to enantiomerically pure compounds. The invention therefore also relates to acylated amines of formula 1 in which X=$NH_2$ and $R_4$=phenyl or p-OH-phenyl and in which $R_1$, $R_2$ and $R_3$ are as defined above.

The acylation is preferably carried out at a high pH, for example at a pH between 6 and 11, in particular between 8 and 11.

The molar ratio of acyl donor to amine preferably lies between 0.5 and 5, in particular between 1 and 3.

The pH at which the hydrolysis is carried out preferably lies between 4 and 8, in particular between 5 and 8.

The temperature at which the acylation and hydrolysis is carried out is not particularly critical and lies for example between 0 and 50° C., in particular between 0 and 30° C. Preferably the reactions are carried out at room temperature.

In the method according to the invention a Pen-G acylase originating from *Alcaligenes faecalis* is applied, for example *Alcaligenes faecalis* originating from ATCC 19018. The enzyme can optionally be applied in immobilized form.

Such enzymes are obtainable via generally known technologies. The enzyme preparation such as is used with the present invention is not limited by purity and the like and can be both a crude enzyme solution and a purified enzyme, but it can also consist of (permeabilized and/or immobilized) cells that have the desired activity, or of a homogenate of cells with such an activity. The enzyme can also be used in an immobilized form or in a chemically modified form. The invention is in no way limited by the form in which the enzyme is used for the present invention. Within the framework of the invention naturally also an enzyme or a variant thereof can be used which originates from a genetically modified microorganism, whether or not with application of recombinant DNA techniques.

The acylation and the hydrolysis are preferably carried out in water, optionally mixed with an organic solvent, for example acetonitrile or a lower (C1–C5) alcohol.

The invention can be applied particularly well for the splitting of amines (for example as shown in following diagram). For that purpose in one embodiment first a mixture of the enantiomers of the amine to be split according to the invention is acylated enantioselectively with a Pen-G acylase with the aid of a phenylacetic acid derivative, subsequently the enantiomerically enriched acylated amine is separated from the non-acylated amine, and then the enantiomerically enriched, acylated amine according to the invention is hydrolyzed, a mixture of enantiomerically enriched amine and phenylacetic acid corresponding to the applied phenylacetic acid derivative being formed, the enantiomeric excess of the amine having been increased again relative to the enantiomeric or diastereomeric excess of the acylated amine. If for example phenylglycine amide is applied as acyl donor it is furthermore possible, if desired, in order to obtain an amine with a still higher enantiomeric excess, to first crystallize the intermediate product acylated amine of formula 1, thus further increasing the diastereomeric excess of the acylated amine.

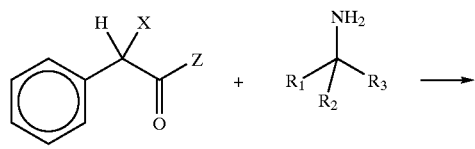

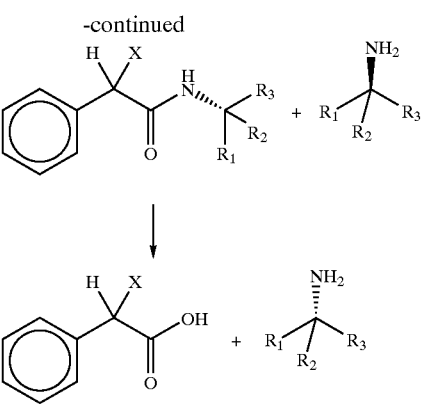

The separation of the acylated amine and the non-acylated amine can be carried out in a known way, for example via crystallization, extraction or phase separation, depending on the reaction conditions and the chosen substrate.

In another embodiment for the splitting of amines first a mixture of the enantiomers is acylated enantioselectively, for example chemically or enzymatically with the aid of a lipase in an organic solvent and the acylated amine is separated from the non-acylated amine, and subsequently the acylated amine according to the invention is hydrolized with the aid of an enzyme derived from *Alcaligenes faecalis*.

The invention is explained further on the basis of the following examples without however being limited thereby.

EXAMPLES

Example I

Enzymatic Acylation of (R, S)-1-phenylethylamine with Phenylacetamide with the Aid of *A. Faecalis*.

0.40 g (3.3 mmol) (R, S)-1-phenylethylamine was added to 14 ml of water and the pH was brought to 10 with 3N HCl. Subsequently 0.41 g (3.0 mmol) phenylacetamide was added, followed by a small quantity of water to bring the total reaction volume to 15 ml. The reaction mixture was subsequently stirred for 5 minutes, in which process the (R, S)-1-phenylethylamine went into solution and the temperature of the reaction mixture was brought to 25° C. Subsequently 0.078 ml of a solution of *A. Faecalis* (2.3 $10^{-4}$ M, 1060 U/ml; 1U is defined as the quantity of enzyme that per minute hydrolyzes 1 μmole Pen-G at pH=8.0 and T=34° C.) in water was added. During the enzymatic acylation the pH was kept at 10 with a 2M KOH solution. After 50 minutes around 50% acylation was achieved. The precipitated product was filtered off and washed with 2×2 ml water and dried to constant weight.

Yield: 0.54 g (2.3 mmol, 48%) N-phenylacetyl-(R)-1-phenylethylamine with e.e. 98%, E≈100

Comparative Experiment A

Enzymatic Acylation of (R, S)-1-phenylethylamine with Phenylacetamide with the Aid of *E. Coli*.

0.48 g (4.0 mmol) (R, S)-1-phenylethylamine was added to 20 ml water and the pH was brought to 10 with 3M $H_2SO_4$. Subsequently 1.35 g (10.0 mmol) phenylacetamide was added and the temperature of the reaction mixture brought to 0° C. Subsequently 0.1 ml of a solution of *E. Coli* (5.7 $10^{-4}$ M, 1560 U/ml) in water was added. During the enzymatic acylation the pH was kept at 10 with a 2M NaOH solution. The reaction was followed in time with the aid of chiral HPLC analysis. $E \approx 5$ was found for the N-phenylacetyl-(R)-1-phenylethylamine.

Example II

Enzymatic Deacylation of N-phenylacetyl-(R, S)-1-phenylethylamine with the Aid of A. Faecalis 0.33 g (1.4 mmol) N-phenylacetyl (R, S)-1 phenylethylamine was added to 10 ml water/methanol (80:20 V/V) at 25° C. and the pH was brought to 7.5. Subsequently 2.0 µl of a solution of A. Faecalis (2.3–$10^{-4}$ M, 1060 U/ml) in water was added. During the enzymatic acylation the pH was kept at 7.5 with a 3M $H_2SO_4$ solution. The reaction was followed in time with the aid of chiral HPLC analysis. After 1 hour around 50% conversion was found with $E \approx 300$.

Comparative Experiment B

Enzymatic Deacylation of N-phenylacetyl-(R, S)-1-phenylethylamine with the Aid of E. Coli 0.33 g (1.4 mmol) N-phenylacetyl (R, S)-1 phenylethylamine was added to 10 ml water/methanol (80:20 V/V) at 25° C. and the pH was brought to 7.5. Subsequently 0.5 µl of a solution of E. Coli (5.7$^{-4}$ M, 1560 U/ml) in water was added. During the enzymatic acylation the pH was kept at 7.5 with a 3M $H_2SO_4$ solution. The reaction was followed in time with the aid of chiral HPLC analysis. After 8 hours around 50% conversion was found with $E \approx 10$.

Example III

Enzymatic Acylation of (R, S)-2-amino-4-phenylbutane with Phenylacetamide with the Aid of A. Faecalis.

0.33 g (2.2 mmol) (R, S)-2-amino-4-phenylbutane and 0.37 g (2.7 mmol) phenylacetamide was added to 10 ml water. Subsequently the pH was brought to 10 with 3 N HCl and a small quantity water was added to bring the total reaction volume to 12 ml. The reaction mixture was subsequently stirred for 5 minutes, during which time the temperature of the reaction mixture was brought to 25° C. Subsequently 0.096 ml of a solution of A. Faecalis (2.3 $10^{-4}$ M, 1060 U/ml) in water was added. During the enzymatic acylation the pH was kept at 10 with a 2M KOH solution. After 8–9 minutes around 50% acylation was achieved. The precipitated product was filtered off and washed with 2×2 ml water and dried to constant weight. Yield: 0.27 g (1.0 mmol, 45% ) N-phenylacetyl-(R)-2-amino-4-phenylbutane, with e.e=98%, $E \approx 100$

Comparative Experiment C

Enzymatic Acylation of (R. S)-2-amino-4-phenylbutane with Phenylacetamide with the aid of E. Coli.

0.60 g (4.0 mmol) (R, S)-2-amino-4-phenylbutane was added to 20 ml water and the pH was brought to 10 with 3M $H_2SO_4$. Subsequently 1.35 g (10.0 mmol) phenylacetamide was added and the temperature of the reaction mixture was brought to 0° C. Subsequently 0.1 ml of a solution of E. Coli (5.7 $10^{-4}$M, 1560 U/ml) in water was added. During the enzymatic acylation the pH was kept at 10 with a 2M NaOH solution. The reaction was followed in time with the aid of chiral HPLC analysis. An $E \approx 2$ was found for the N-phenylacetyl-(R)-2-amino-4-phenylbutane.

Example IV

Enzymatic Deacylation of N-phenylacetyl (R, S) 1,1-1-trifluoro-2-amino-3-phenylpropane with the Aid of A. Faecalis 0.12 g (0.4 mmol) N-phenylacetyl (R, S)-1,1-1-trifluoro-2-amino-3 phenylpropane was added to 10 ml water/methanol (70:30 V/V) at 25° C. and the pH was brought to 7.5. Subsequently 1.7 µl of a solution of A. Faecalis (2,3 $10^{-4}$ M, 1060 U/ml) in water was added. During the enzymatic acylation the pH was kept at 7.5 with a 3M $H_2SO_4$ solution. The reaction was followed in time with the aid of chiral HPLC analysis. After 2 hours around 50% conversion was found with $E \approx 100$.

Comparative Experiment D

Enzymatic Deacylation of N-phenylacetyl-(R, S)-1,1,1-trifluoro-2-amino-3-phenylpropane with the Aid of E. Coli 0.12 g (0.4 mmol) N-phenylacetyl (R, S)-1,1-1-trifluoro-2-amino-3 phenylpropane was added to 10 ml water/methanol 70:30 V/V) at 25° C. and the pH was brought to 7.5. Subsequently 3.6 µl of a solution of E. Coli (5.7 $10^{-4}$ M, 1560 U/ml) in water was added. During the enzymatic acylation the pH was kept at 7.5 with a 3M $H_2SO_4$ solution. The reaction was followed in time with the aid of chiral HPLC analysis. After 1.5 hours around 50% conversion was found with $E \approx 1.3$.

Example V

Enzymatic Acylation of (R, S)-1-(P-chlorophenyl)ethylamine with Phenylacetamide with the Aid of A. Faecalis 0.31 g (2.0 mmol) (R, S)-1-(P-chlorophenyl)ethylamine and 0.22 g (1.6 mmol) phenylacetamide was added to 17 ml water and 2 ml methanol. The pH was brought to 10 with 3N HCl, after which water was added to the reaction mixture to give a final volume of 20 ml. The reaction mixture was then stirred for 5 minutes with the temperature of the reaction mixture being brought to 25° C. Subsequently 0.148 ml of a solution of A. Faecalis (2.3 $10^{-4}$ M, 1060 U/ml) in water was added. During the enzymatic acylation the pH was kept at 10 with a 2M KOH solution. After 10 minutes around 50% acylation was achieved. After 40 minutes an enantiomeric excess of ee=99.3% was measured for the product with the aid of chiral HPLC, which corresponds to E * 1600

Comparative Experiment E

Enzymatic Acylation of (R, S)-1-(p-chlorophenyl)ethylamine with Phenylacetamide with the Aid of E. Coli Under comparable conditions as described in example I, 0.19 g (1.2 mmol) (R, S)-1-(P-chlorophenyl)ethylamine and 0.13 g (0.96 mmol) phenylacetamide was added to 10 ml water and 1.2 ml methanol. The pH was brought to 10 with 3N HCl, after which water was added to the reaction mixture to give a final volume of 12 ml. The reaction mixture was then stirred for 5 minutes with the temperature of the reaction mixture being brought to 25° C. Subsequently 0.330 ml of a solution of E. Coli (5.7 $10^{-4}$ M, 1560 U/ml) in water was added. During the enzymatic acylation the pH was kept at 10 with a 2M KOH solution. After 40 minutes around 0.5% acylation was measured.

Example VI

Enzymatic Acylation of (R,S)-1-(2-Naphthyl)ethylamine (0.2 M) with Phenylacetamide (0.2 M) as Acyl Donor at Constant pH 10 Catalyzed by Pen-G Acylase from *A. faecalis* (1.1 µM)

0.274 g of (R,S)-1-(2-naphthyl)ethylamine (MW 171) was added to the 7.5 ml of water and pH was adjusted to 10 by 3 N HCl; 0.216 g of phenylacetamide (MW 135) was added to the solution and some additional amount of water was added in order to have 7.96 ml of the final solution. Reaction mixture was mixed 5–10 min in a thermostated cell in order to reach fixed temperature (25° C.) and to get saturated solution of reagents, and 39 µl of initial enzyme solution ($2.3 \cdot 10^{-4}$ M PA-*A.faecalis*)) was added to start enzymatic acylation. Reaction was performed in a cell of a pH-stat at a constant pH value (pH 10) titrating reaction mixture by KOH solution.

Stereospecificity of acylation 250(R), Synthesis rate 240 $s^{-1}$, initial S/H ratio–6.5. In 20 min conversion reached 46.8%; ee of the product–98.1%.

Comparative Example F

Enzymatic Acylation of (R,S)-1-(2-Naphthyl)ethylamine (0.2 M) with Phenylacetamide (0.2 M) as Acyl Donor at Constant pH 10 Catalyzed by Pen-G Acylase from *E. coli* (10 µM)

0.274 g (R,S)-1-(2-naphthyl)ethylamine (MW 171) was added to the 7.5 ml of water and pH was adjusted to 10 by 3 N HCl; 0.216 g of phenylacetamide (MW 135) was added to the solution and some additional amount of water was added in order to have 7.735 ml of the final solution. Reaction mixture was mixed 5–10 min in a thermostated cell in order to reach fixed temperature (25° C.) and to get saturated solution of reagents, and 265 µl of initial enzyme solution ($3.0 \cdot 10^{-4}$ M PA-*E.coli*)) was added to start enzymatic acylation. Reaction was performed in a cell of a pH-stat at a constant pH value (pH 10) by titrating reaction mixture by KOH solution.

Stereospecificity of acylation 22(R), Synthesis rate~11 $s^{-1}$, initial S/H ratio–0.42. Enzyme lost all activity in 15 min; by this time only about 18% acylation of amine was reached and ee of the product was 89.7%.

Example VII

Enzymatic Acylation of (R, S)-phenylglycinol with Phenylacetamide with the Aid of *A. Faecalis*

0.41 g (3.0 mmol) (R, S)-phenylglycinol and 0.51 g (3.7 mmol) phenylacetamide was added to 15 ml water. The pH was brought to 10. The reaction mixture was then stirred for 5 minutes with the temperature of the reaction mixture being brought to 25° C. Subsequently 0.144 ml of a solution of *A. Faecalis* ($1.5 \ 10^{-4}$ M, 690 U/ml) in water was added. During the enzymatic acylation the pH was kept at 10 with a 2M KOH solution. After 45 minutes a maximum conversion of 50.6% was measured with the aid of HPLC. An accurate estimate of this very high E-value is not possible on the basis of these experiments. Therefore the E-value has been determined on the basis of the kinetic constants of the separate enantiomers (see example VIII).

Example VIII

Determination of the E-value of the Acylation of (R, S) Phenylglycinol with Phenylacetamide and (D) Phenylglycine Amide with the Aid of *A. Faecalis* and *E. Coli* on the Basis of Determination of the Kinetic Constants of the Separate Enantiomers 0.069 g (0.5 mmol) (R) or (S) phenylglycinol and 0.14 g (1.0 mmol) phenylacetamide or 0.15 g (1.0 mmol) (D) phenylglycine amide was added to approximately 4 ml water. The pH was brought to 9.5 to 10 with 3N HCl, after which the volume was made up to a final volume of 5.0 ml. The reaction mixture was then incubated for 5 minutes at 25° C. The reaction was started by addition of 0.05 ml of a solution of *A. Faecalis* ($1.5 \ 10^{-4}$ M, 690 U/ml) or 0.3 ml of a solution of *E. Coli* ($3.3 \ 10^{-4}$ M, 900 U/ml). During the enzymatic acylation the pH was kept at 9.5 to 10 with a 2 M KOH solution. The E-values of the various reactions were determined on the basis of the kinetic constants via measurement of the initial acylation rates of the separate enantiomers.

| Pen-G acylase | Acyl donor | S/H ratio | Activity (sec-1) | E-value |
|---|---|---|---|---|
| *A. Faecalis* | Phenylacetamide | 2.7 | 115 | 270 |
|  | (D)-phenylglycineamide | 4.6 | 160 | 2000 |
| *E. Coli* | phenylacetamide | 0.15 | 2.8 | 40 |
|  | (D)-phenylglycineamide | 0.75 | 5.7 | 1600 |

What is claimed is:

1. A method for the preparation of an enantiomerically enriched acylated amide of formula 1,

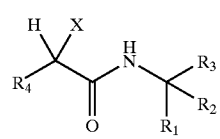

1)

wherein $R_4$ is a substituted or unsubstituted phenyl group,
X is H, OH, $NH_2$, NHOH, F, Cl, Br, $NO_2$, alkyl or alkoxy with 1–3 C-atoms, and
each of $R_1$, $R_2$, $R_3$ is different from the other two, and each is independently H, CN, alkoxy, alkyl, cycloalkyl, aryl, alkylaryl, arylalkyl, or a cyclic or noncyclic heteroalkyl or heteroaryl group with one or more N, O or S atoms, each of which may be optionally substituted with halo, hydroxy, alkoxy, aryloxy, thio, alkylthio, arylthio, cyano, nitro, amino, dialkylamino, or amido;

wherein a phenylacetic acid derivative of formula 2,

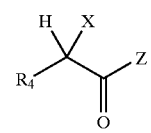

2)

wherein $R_4$ and X are as defined above, and
Z is a C1–C7 alkoxy group; $NR_6R_7$, where $R_6$ and $R_7$ are each independently H, a substituted or unsubstituted alkyl, cycloalkyl, or aryl group; $NHNH_2$; or $NHOR_8$, where $R_8$ is H, or a C1–C7 alkyl group, is contacted with a mixture of enantiomers of the amine $H_2NCR_1R_2R_3$, where $R_1$, $R_2$ and $R_3$, are as defined above,
in the presence of a Pen-G acylase originating from *Alcaligenes faecalis*.

2. The method of claim 1, wherein at least one of the groups $R_1$, $R_2$ and $R_3$ represents a heteroaryl, aralkyl or alkaryl group.

3. The method of claim 1, wherein the pH lies between 6 and 11.

4. The method of claim 1, further comprising the step of contacting said enantiomerically enriched acylated amide of formula 1 with a Pen-G acylase originating from *Alcaligenes faecalis* to form an enantiomerically enriched amine of formula $H_2NCR_1R_2R_3$, wherein each of $R_1$, $R_2$ and $R_3$ are as defined in claim 1.

5. The method of claim 4, wherein the pH lies between 4 and 8.

6. The method of claim 4, further comprising separating the compound of formula 1 from the amine of formula $H_2NCR_1R_2R_3$.

7. The method of claim 1, wherein the phenylacetic acid derivative of formula 2 is an enantiomerically enriched derivative of phenylglycine.

8. A compound of the formula 1,

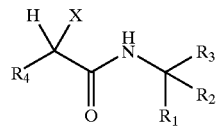

1 wherein X is $NH_2$, $R_4$ is phenyl or p-OH-phenyl, and each of $R_1$, $R_2$, $R_3$ is different from the other two, and is independently H, CN, alkoxy, alkyl, cycloalkyl, aryl, alkylaryl, arylalkyl, or a cyclic or noncyclic heteroalkyl or heteroaryl with one or more N, O or S atoms, each of which may be optionally substituted with halo, hydroxy, alkoxy, aryloxy, thio, alkylthio, arylthio, cyano, nitro, amino, dialkylamino, or amido.

9. An acylated amine of claim 8 with a diastereomeric excess>90%.

10. The acylated amine of claim 9 which has a diastereomeric excess>95%.

11. The acylated amine of claim 9 which has a diastereomeric excess>98%.

12. The method of claim 1, wherein said Pen-G acylase is obtained from a wild-type or a genetically modified organism.

13. A method for the preparation of an enantiomerically enriched amine of formula $H_2NCR_1R_2R_3$, each of $R_1$, $R_2$, $R_3$ is different from the other two, and is independently H, CN, alkoxy, alkyl, cycloalkyl, aryl, alkylaryl, arylalkyl; or a noncyclic heteroalkyl or a cyclic or noncyclic heteroaryl with one or more N, O or S atoms, each of which may be optionally substituted with halo, hydroxy, alkoxy, aryloxy, thio, alkylthio, arylthio, cyano, nitro, amino, dialkylamino, or amido, which comprises deacylating an enantiomerically enriched amide of formula 1,

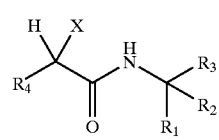

1 wherein $R_1$, $R_2$ and $R_3$ are as defined above, $R_4$ is a substituted or unsubstituted phenyl group, and X is H, OH, $NH_2$, NHOH, F, Cl, Br, $NO_2$, alkyl or alkoxy with 1–3 C-atoms, with a Pen-G acylase originating from *Alcaligenes faecalis*.

14. The method of claim 13, wherein the pH lies between 4 and 8.

15. The method of claim 13, further comprising separating the compound of formula 1 from the amine of formula $H_2NCR_1R_2R_3$.

16. The method of claim 13, wherein compound 1 has a diastereomeric excess>90%.

17. The method of claim 13, wherein compound 1 has a diastereomeric excess>95%.

18. The method of claim 13, wherein compound 1 has a diastereomeric excess>98%.

19. The method of claim 13, wherein said Pen-G acylase is obtained from a wild-type or a genetically modified organism.

20. The method of claim 7, wherein the phenylacetic acid derivative is p-hydroxyphenylglycine.

* * * * *